United States Patent [19]
Schenck

[11] 4,296,066
[45] Oct. 20, 1981

[54] MULTICHAMBER PHOTOREACTOR

[76] Inventor: Günther Schenck, Bismarckstrasse 31, 4330 Mülheim-Ruhr, Fed. Rep. of Germany

[21] Appl. No.: 115,657

[22] Filed: Jan. 28, 1980

Related U.S. Application Data

[63] Continuation-in-part of Ser. No. 923,710, Jul. 11, 1978, Pat. No. 4,255,383.

[30] Foreign Application Priority Data

Feb. 5, 1979 [DE] Fed. Rep. of Germany ....... 2904242

[51] Int. Cl.³ .......................... A61L 2/10; A61L 2/16; A61L 2/24
[52] U.S. Cl. ..................................... 422/24; 210/764; 210/765; 250/436; 250/437; 422/28; 422/111
[58] Field of Search .......................... 422/24, 28, 111; 250/527, 432 R, 436, 437; 356/246; 210/60, 64, 63 R, 764, 765

[56] References Cited

U.S. PATENT DOCUMENTS

| | | |
|---|---|---|
| 2,338,388 | 1/1944 | Whitman .......................... 422/24 X |
| 2,588,716 | 3/1952 | Gochenour et al. ............. 422/24 X |
| 4,116,630 | 9/1978 | Meacham, Jr. et al. ............... 422/24 |
| 4,255,383 | 3/1981 | Schenck ............................... 422/24 |

FOREIGN PATENT DOCUMENTS 2735550 2/1979 Fed. Rep. of Germany ........ 422/24

Primary Examiner—Ronald Serwin
Attorney, Agent, or Firm—Howard H. Darbo

[57] ABSTRACT

Various embodiments of photoreactors are disclosed which have at least two irradiation chambers with a window therebetween. Ultraviolet radiation is introduced into one of the chambers at a side opposite the window so that it passes through that chamber, through the window and into the other chamber. The fluid medium to be purified is passed through the chambers and subjected to the radiation while in the chambers. The flow of the medium is through the chambers in series. The chambers are optimized in depth with respect to efficiency in terms of the flow-dose rate. In a two chamber photoreactor traversed by parallel radiation the maximum is at a total absorption of about 70 percent and at an absorption of about 27 percent in the chamber immediately adjacent to the radiation source. In an annular two chamber photoreactor with an elongate radiation source extending along the axis thereof the corresponding data are 45 to 65 percent and 16 to 25 percent, respectively. In an immersion type three chamber photoreactor of analogous configuration the corresponding data are 60 to 80 percent and 14 to 20 percent, respectively.

49 Claims, 4 Drawing Figures

MULTICHAMBER PHOTOREACTOR

RELATED APPLICATION

This application is a continuation-in-part of my co-pending application Ser. No. 923,710, filed July 11, 1978, and entitled MULTICHAMBER PHOTOREACTOR, and now U.S. Pat. No. 4,255,383.

BACKGROUND AND SUMMARY OF THE INVENTION

The invention relates to a process of purifying a fluid medium with a predetermined minimum radiation dose of ultraviolet radiation wherein, at a given location a number n, less than six, of flow paths for said medium are provided in juxtaposition to each other and the incident ultraviolet radiation is first introduced into one of said paths and permitted to escape from said one path into other of said paths. The invention also relates to an apparatus for purifying a fluid medium at a predetermined minimum radiation dose of ultraviolet radiation comprising a flow reactor defining an irradiation volume having two sides and through which volume said medium flows, at least one ultraviolet radiation source positioned to introduce ultraviolet radiation into the medium into said volume at least at one of said sides, and comprising further at a given location within said irradiation volume first means forming windows transparent to ultraviolet radiation and spaced from each other and second means defining one side of said irradiation volume, a total number n, less than six, of successive irradiation chambers and windows being provided through which the radiation will pass from one irradiation chamber to the next.

Such processes and apparatus are described in my co-pending application Ser. No. 923,710. The disclosure of my co-pending application Ser. No. 923,710 filed July 11, 1978, now U.S. Pat. No. 4,255,383, and entitled Multichamber Photoreactor is incorporated herein by reference. The particular advantages gained by combining the effects of the UV radiation on the medium in the different irradiation flow paths are discussed therein with reference to presently used known single chamber photoreactors and with reference to known multichamber photoreactors of different configuration as well as with reference to the significant increase in efficiency achieved by limiting the absorption by the medium in the flow path immediately adjacent to the radiation source to not more than 50 percent and the total absorption in all the flow paths to values increasing with the number of flow paths, for instance to 75 percent, if two flow paths are present.

The present invention is based on the recognition that at a predetermined minimum dose the efficiency in terms of flow-dose rate achievable in a single chamber photoreactor is determined by the depth of the medium therein, said flow-dose rate depending on the volume of the irradiation chamber and on the effective irradiation intensity. If the flow-dose rate at the required minimum dose M (in milliwatt seconds per cm$^2$) results from the rate of flow Q (in m$^3$/h) and from the irradiation intensity (in milliwatts per cm$^2$), the flow-dose rate Q·M is a function of the volume V of the medium and the radiation dose E $$Q\text{-}M = f(V, E)$$

Therein, Q-M is the flow-dose rate at the required minimum dose M, V is the volume of the irradiation chamber, and E is the radiation intensity. Calculations will have to be based on the minimum radiation intensity effective within the volume V of the reactor chamber and not on the intensity of the radiation entering the reactor. The volume of the reactor chamber increases and the effective radiation intensity decreases with increasing depth d $$Q\text{-}M = V(d)\cdot E(d)$$

In accordance with the rules of differential calculus a maximum for the flow-dose rate will result therefrom $$\frac{d(Q-M)}{d(d)} = \frac{d(V(d)\cdot E(d))}{d(d)}$$
$$0 = V(d)\cdot \frac{d(E(d))}{d(d)} + E(d)\cdot \frac{d(V(d))}{d(d)}$$
$$V(d)\cdot \frac{d(E(d))}{d(d)} = -E(d)\cdot \frac{d(V(d))}{d(d)}$$

The volume of the reactor chamber is $$V(d) = d\cdot F$$

F being the face through which the radiation enters. The effective radiation intensity will be that radiation intensity which remains after the incident radiation has passed through a depth d of the medium to be irradiated.

$$E_d = E_o\cdot 10^{-\epsilon\cdot d} \text{ bzw. } E_d = E_o\cdot e^{-kd}$$

For a single chamber photoreactor traversed by parallel radiation a maximum in the flow-dose rate will result therefrom for $$-d\cdot F\cdot E_o\cdot k\cdot e^{-kd} = -F\cdot E_o\cdot e^{-kd}$$

i.e. $d\cdot k = 1$ and $d\cdot \ln T = 1$, respectively,
and $\epsilon\cdot d = \log e$ and $d\cdot \log T = \log e$, respectively.

Therein, k is the extinction coefficient related to the base e of the medium to be irradiated at a wavelength of 254 nm which forms the basis for the entire wavelength range of the effective UV radiation; T is the UV transmission of the medium to be irradiated as measured in a 1 cm cuvette, also at a wavelength of 254 nm; $\epsilon$ is the specific decadic extinction coefficient. The product $\epsilon\cdot d$ usually is termed extinction. In this context "absorption" is the portion A of the incident radiation intensity $E_o$ absorbed in the depth d of the medium and resulting from $A = E_o - E_d$ according to the Lambert Beer Law of Absorption and which may also be expressed in percent of the incident radiation intensity $E_o$.

In the case of a single chamber photoreactor traversed radially by radiation directed outwardly from the interior, the irradiation chamber being arranged coaxially with respect to an envelope tube having the radius $r_i$ and surrounding the radiation source, there is $$V = (r_i+d)^2 - \pi r_i^2 = \pi\cdot d\,(2r_i+d)$$

and $$E_d = \frac{r_i}{r_i + d}\cdot E_o\cdot 10^{-\epsilon\cdot d} \text{ and } \frac{r_i}{r_i + d}\cdot E_o\cdot e^{-kd},$$

respectively.
Therefrom is obtained $$V(d) \cdot E(d) = \pi \cdot d \cdot \frac{2r_i + d}{r_i + d} \cdot E_o \cdot e^{-kd}$$

While complete differentiation of the foregoing expression will result in a complex expression, an approximative consideration shows that the quotient will only have small influence on the slope of the flow-dose rate function and may be approximately accounted for within the usual values of $r_i$ in the exponent. Thus $$V(d) \cdot E(d) = d \cdot F \cdot E_o \cdot e^{-Kd}$$

The maximum of the flow-dose rate will be at $dK=1$. The optimized annular photoreactor and the optimized photoreactor traversed by parallel radiation are interrelated by $K=k \cdot \alpha$ so that the maximum flow-dose rate for the first one will exist at $dK=1/\alpha$, which empirically is found to be $dk=0.826$.

The aforementioned single chamber photoreactors thus have a maximum in the flow-dose rate at a depth d at which the intensity of the effective radiation $E_o$ incident into the reactor has decreased to $e^{-1}$, i.e. to 36.8 percent, in the case of parallel radiation and to $e^{-0.826}$, i.e. to 43.7 percent, in the case of radially directed radiation. With smaller depths the flow-dose rate will deteriorate because of imperfect utilization of the available radiation intensity. With higher depths the flow-dose rate will deteriorate because of the increasing contribution by partial volumina exposed to only small effective radiation intensities. In other words, a single chamber photoreactor having a predetermined depth d will put the UV radiation incident from the radiation source to optimum use only for media within a relatively narrowly limited range of UV transmissions.

The problem to be solved by the invention is to provide for a process and for an apparatus of the kind initially mentioned permitting optimum utilization of the incident radiation. Such a reactor should be designed, if possible, so as to provide for optimum utilization of the UV radiation over a wide range of UV Transmissions of the media to be irradiated or, respectively, at least within the variation in the UV transmission of the medium to be irradiated. Thereby, specifically in connection with water disinfection, should be ensured that the rate of flow of the medium in the irradiation chamber immediately adjacent to the radiation source is sufficient to prevent depositions to occur even under the action of high radiation intensities.

Said problem is solved by the characterizing features as stated in the claims. Advantageous designs and further developments of the invention are characterized by the features in the subclaims. Particularities thereof will be discussed in connection with the embodiments.

Embodiments of the apparatus according to the invention are shown in the drawings and will be explained and described in detail hereinbelow.

DESCRIPTION OF SPECIFIC EMBODIMENTS

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

Figure 1:
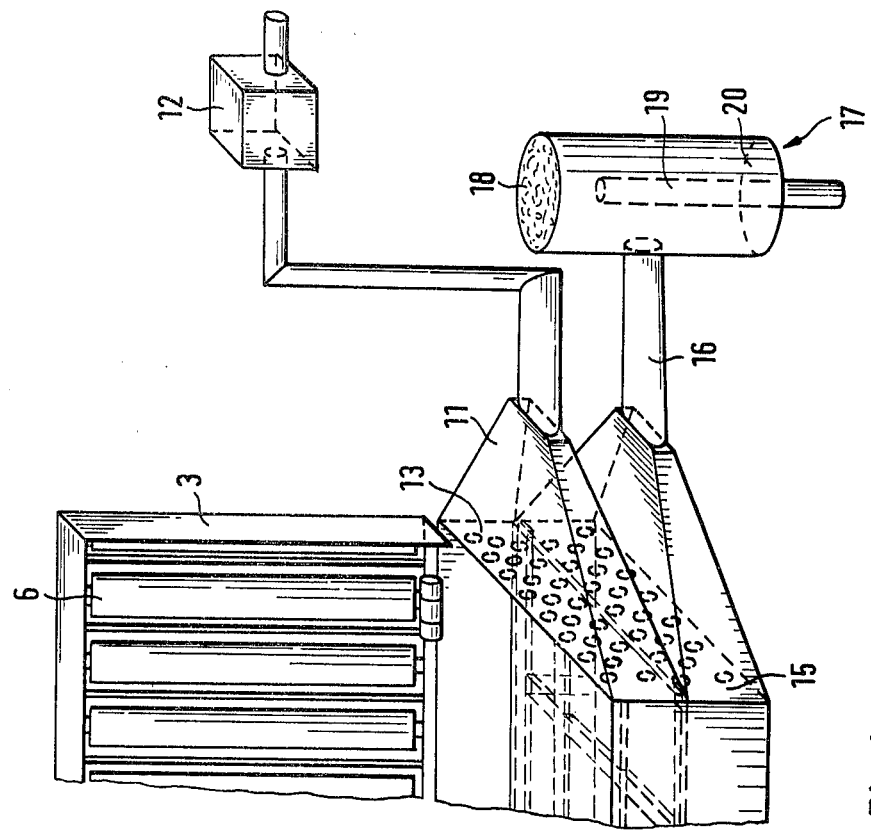
FIG. 1 is an isometric view of a first embodiment of a multichamber photoreactor according to the invention.

FIG. 1 illustrates a two-chamber photoreactor 1 including a trough-like container 2. A cover 3 is pivotably hinged to the container by hinges 4. A latch or the like, not shown, is employed to retain the cover in the closed position. Container 2 is made of metal like stainless steel. It also may be manufactured from any other ultraviolet resistant material meeting other requirements, as for instance food regulations (stoneware, enamel coated sheet metal, etc.). Secured to the inside of cover 3 are a series of paraboloidal reflectors arranged in parallel with respect to each other and provided with highly ultraviolet reflective surfaces. Ultraviolet lamps 6 are placed within the reflectors. The reflectors and lamps are normal with respect to the direction of flow of the fluid medium through container 2 in such a way that the flow cross-section of container 2, including the regions along the edges thereof, are uniformly irradiated. For disinfections water-cooled, antimony doped, high pressure xenon lamps will be employed; alternatively, low pressure mercury lamps of known design also may be used. For purification in the presence or in the absence of oxidizing agents, high pressure mercury lamps or other radiation sources of suitable emission ranges may be employed. The latch or cover is provided with a safety switch by means of which lamps 6 will become automatically switched off when the cover is opened.

Trough-like container 2 is subdivided along the direction of flow by silica glass plates 7 to form two irradiation chambers 8, 9 with the planes forming a window, transparent to ultraviolet radiation, therebetween. Lower irradiation chamber 9 is limited to a fixed depth of 2 cm by the positioning of silica glass plates 7 while the depth of the medium in upper irradiation chamber 8 may be varied by means of level controller 17 subsequently described. Silica glass plates 7 are supported on a removably frame 10 made of stainless steel. The plates are sealingly secured to frame 10 which in turn is sealingly secured to the interior walls of container 2 by means of a cement resistant to ultraviolet radiation. Instead of by cement sealing may also be obtained with a preformed and ultraviolet-resistant gasket.

Irradiation chambers 8 and 9 communicate with each other at their respective ends remote from the input and outlet of trough-like container 2. Upper irradiation chamber 8 is connected to a flow rate limiter 12 via supply conduit 11. The flow rate limiter serves to limit the flow rate to a predetermined maximum admissible value independent of the prevailing input pressure (flow rate limiters of such kind are for instance sold by the Eaton Corporation, Controls Division, 191 East North Avenue, Carol Stream, Ill. 60187). Supply conduit 11 opens into irradiation chamber 8 through perforated plate 13 constituting a balancing element to create a uniform flow pattern across the entire width of irradiation chamber 8. Irradiation chamber 9 opens into a discharge conduit 16 through a similar perforated plate 15 which also acts to balance the flow pattern. Discharge conduit 16 includes the level controller 17.

Perforated plates 13, 15 are made of material resistant to ultraviolet radiation and the medium flowing through the plates. Also, the plates should not give off detrimental contaminants to the medium passing therethrough. Such material may be stainless steel, coated metal, plastic, ceramic, quartz, glass. The width of the perforation will be such that flow-through will not be significantly impaired but that a uniform pattern of flow over the entire passage area is obtained. For achieving this purpose the perforation may be composed of circular holes, but other designs like slots, etc., will also be suitable. The perforated plates 13, 15 are sealingly cemented to the trough-like container 2 at one of their sides and to correspondingly formed transitional sections in supply conduit 11 and discharge conduit 16, respectively, at the other side.

Level controller 17 has an interior tube 19, which is sealingly and vertically movably guided in an open top vessel 20, and forms the outlet of trough-like container 2. This vessel has a protective cover 18 permeable to air made for instance of cotton to prevent the entry of impurities. By vertical adjustment of the interior tube 19 the depth of the medium in the flow reactor may be adjusted in upper irradiation chamber 8 in adaptation to the respective optical density of said medium.

The flow-dose rate of such a two chamber photoreactor traversed by parallel radiation is composed from contributions originating in each one of the irradiation chambers, i.e.

$$Q\text{-}M = d_1 F \cdot E_o \cdot 10^{-\epsilon d_1} + d_2 F \cdot E_o \cdot 10^{-\epsilon(d_1+2)}$$

If for the purpose of calculation the total depth $d_1 + d_2 = D$ is inserted, Q-M will be $$Q\text{-}M = d_1 F \cdot E_o \cdot e^{-kd_1} + (D - d_1) E_o \cdot e^{-kD}$$

Partial differentiation of this equation with respect to $d_1$ and D will yield $$d_1 k = 1 - e^{-k(D-d_1)}$$

and $Dk = 1 + d_1 k$ for the maximum flow-dose rate.

Therefrom the maximum in the flow-dose rate is shown to exist at a total extinction of
$Dk = 1.632$ or $D \cdot \epsilon = 0.708$, respectively,
and at an extinction of
$d_1 k = 0.632$ or $d_1 \cdot \epsilon = 0.273$, respectively,
in the irradiation chamber 8 immediately adjacent to the radiation source 6, any attenuation by the quartz glass plates 7 being neglected. The extinction $d_2 \cdot \epsilon$ in the other chamber resulting as the difference between the two extinction values as given before corresponds to the extinction in a single chamber photoreactor of the same design optimized in terms of the flow-dose rate.

Two-chamber photoreactor 1 comprises 20 low pressure mercury lamps (15 W, NN 15/44 Original Hanau Quarzlampen GmbH, Hanau, Federal Republic of Germany) positioned normally with respect to the direction of flow and equally spaced from each other over the length, 80 cm, of irradiation chambers 8, 9. Each lamps is placed in a reflector associated therewith. The smallest possible distance is maintained between adjacent lamp-reflector combinations. The total flux of ultraviolet radiation impinging on the surface of the medium (considering a maximum of 45 percent reflection losses and unavoidable losses in the edge regions) will then amount to about 60 watts (W) with a mean radiation intensity of $E = 25$ mW/cm². Table 1 shows the flow-dose rate Q-M (m³/h) of two chamber photoreactor 1 having a total depth of $D = d_1 + d_2 = 4.6$ cm as resulting from calculation for a medium having a UV transmission of T (1 cm) = 0.7 ($\epsilon = 0.155$ and ln T = 0.357) as a function of the depth $d_1$ for a minimum dose of 40 milliwatt seconds per cm². The maximum of the flow-dose rate is in the range of $d_1 = 1.6$ to 1.8 cm corresponding to $\epsilon \cdot d_1 = 0.248$ to 0.279. The table also gives the practically important UV transmissions $T_1$ and $T_2$ of the medium in the irradiation chambers 8 and 9, respectively.

TABLE 1

Flow-dose rate Q-40 (m³/h) of a two chamber photoreactor traversed by parallel radiation for variable partial depths $d_1$ and $d_2$; $d_2 + d_2 = 4.6$ cm; UV transmission T (1 cm) = 0.7; $T_1 \cdot T_2 = 0.196$.

| $d_1$ cm | $d_2$ cm | Q-40 m³/h | $T_1$ | $T_2$ |
|---|---|---|---|---|
| 1.0 | 3.6 | 12.6 | 0.7 | 0.280 |
| 1.2 | 3.4 | 13.0 | 0.652 | 0.301 |
| 1.4 | 3.2 | 13.2 | 0.607 | 0.323 |
| 1.6 | 3.0 | 13.4 | 0.565 | 0.347 |
| 1.8 | 2.8 | 13.4 | 0.526 | 0.372 |
| 2.0 | 2.6 | 13.3 | 0.490 | 0.4 |
| 2.2 | 2.4 | 13.2 | 0.456 | 0.430 |
| 2.4 | 2.2 | 13.0 | 0.425 | 0.461 |
| 2.6 | 2.0 | 12.7 | 0.396 | 0.495 |
| 2.8 | 1.8 | 12.4 | 0.368 | 0.532 |
| 3.0 | 1.6 | 12.0 | 0.343 | 0.571 |
| 3.2 | 1.4 | 11.6 | 0.319 | 0.614 |
| 3.4 | 1.2 | 11.2 | 0.297 | 0.659 |

60 watts ultraviolet radiation of 254 nm; 30 · 80 = 2400 cm² area of irradiation; mean radiation intensity E = 25 milliwatts per cm².

As will follow from Table 1, the flow-dose rate in the range of the maximum will vary by less than ±2 percent, if the depth is changed by ±15 percent. This implies that no specific requirements will have to be met with respect to precision in the assembly. It further means that the effect of variations in the UV transmission of the medium on the flow-dose rate within a certain range has only little or, under certain conditions, negligible significance. Thus, a two chamber photoreactor 1 having a depth of $d_1 = 1.8$ cm in irradiation chamber 8 and of $d_2 = 2.8$ cm in irradiation chamber 9 may be utilized for media having UV transmissions in the range of T (1 cm) 0.6 to 0.9 while an analogous photoreactor with corresponding depths of $d_1 = 0.9$ cm and $d_2 = 1.4$ cm may be used for media having UV transmissions in the range of T (1 cm) 0.35 to 0.75.

The flow-dose rate data Q-40 as above do not imply a statement about possible flow rates as long as the smallest cross-sections or highest rates of flow within the chambers are not considered simultaneously. The two chamber photoreactor as described above in Table 1 will not permit high flow rates at free flow of the medium. Therefore, such reactors will be employed for low flow rates at higher minimum doses, but it may also be possible to use lower-powered radiation sources.

Following Table 2 shows correspondingly the flow-dose rate Q-200 in m³/h of two chamber photoreactor 1 for a medium having a UV transmission of T (1 cm) = 0.7 at different depths $d_1$ and $d_2$ and at constant total depth $d_1 + d_2$ as well as the UV transmission of irradiation chambers 8 and 9.

TABLE 2

Flow-dose rate Q-200 (m³/h) of a two chamber photoreactor traversed by parallel radiation for variable partial depths $d_1$ and $d_2$; $d_1+d_2=4.6$ cm; UV transmission T (1 cm)=0.7; $T_1 \cdot T_2 = 0.196$

| $d_1$ cm | $d_2$ cm | Q-200 m³/h | $T_1$ | $T_2$ |
|---|---|---|---|---|
| 1.0 | 3.6 | 2.52 | 0.7 | 0.280 |
| 1.2 | 3.4 | 2.6 | 0.652 | 0.301 |
| 1.4 | 3.2 | 2.64 | 0.607 | 0.323 |
| 1.6 | 3.0 | 2.69 | 0.565 | 0.347 |
| 1.8 | 2.8 | 2.69 | 0.526 | 0.372 |
| 2.0 | 2.6 | 2.66 | 0.490 | 0.4 |
| 2.2 | 2.4 | 2.64 | 0.456 | 0.430 |
| 2.4 | 2.2 | 2.6 | 0.425 | 0.461 |
| 2.6 | 2.0 | 2.54 | 0.396 | 0.495 |
| 2.8 | 1.8 | 2.48 | 0.368 | 0.532 |
| 3.0 | 1.6 | 2.4 | 0.343 | 0.571 |
| 3.2 | 1.4 | 2.32 | 0.319 | 0.614 |
| 3.4 | 1.2 | 2.24 | 0.297 | 0.659 |

60 watts ultraviolet radiation of 254 nm; 30 · 80 = 2400 cm² area of irradiation; mean radiation intensity E = 25 milliwatts per cm².

Figure 2:
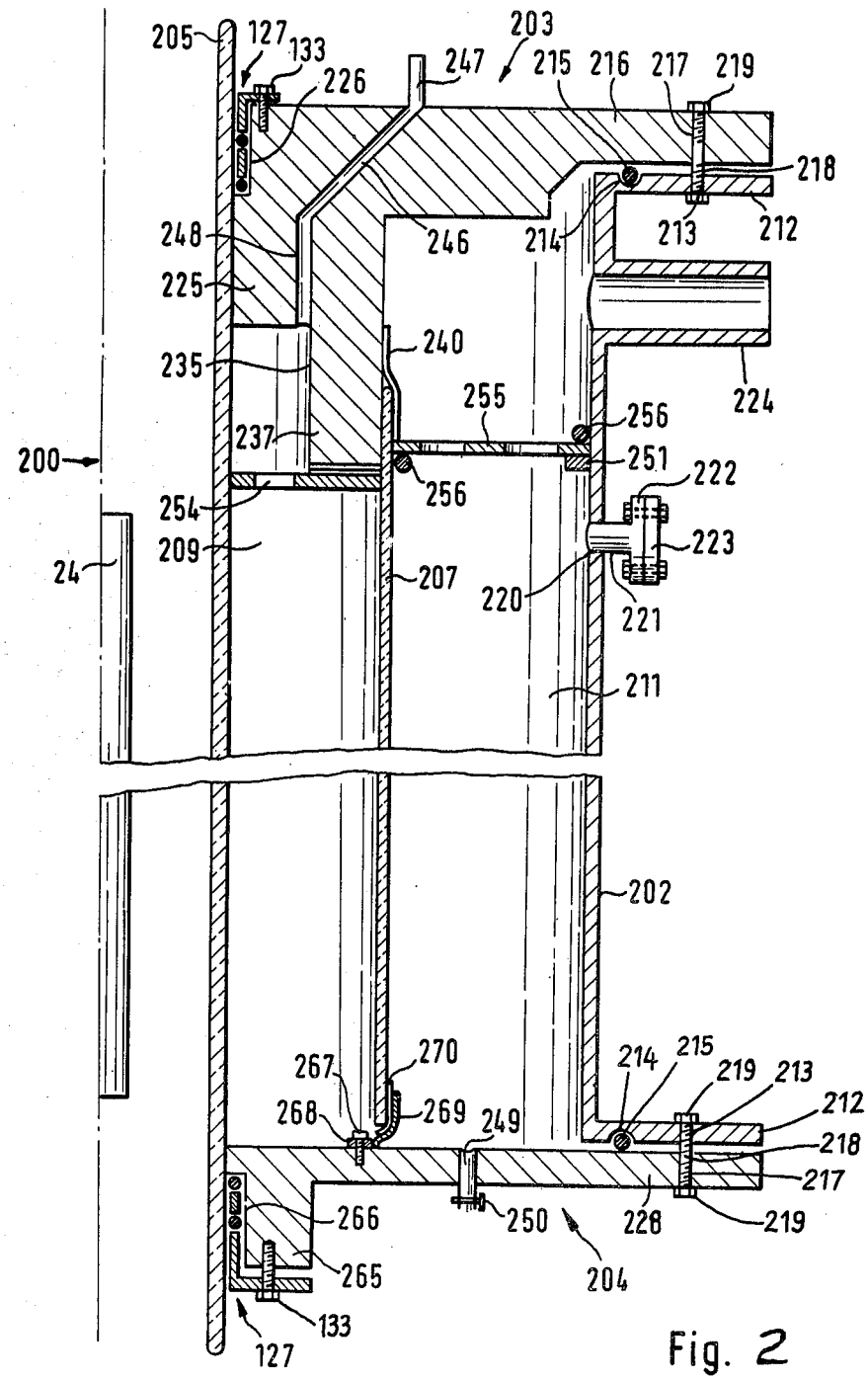
FIG. 2 is a longitudinal section of a second embodiment of the multichamber photoreactor according to the invention.
Figure 3:
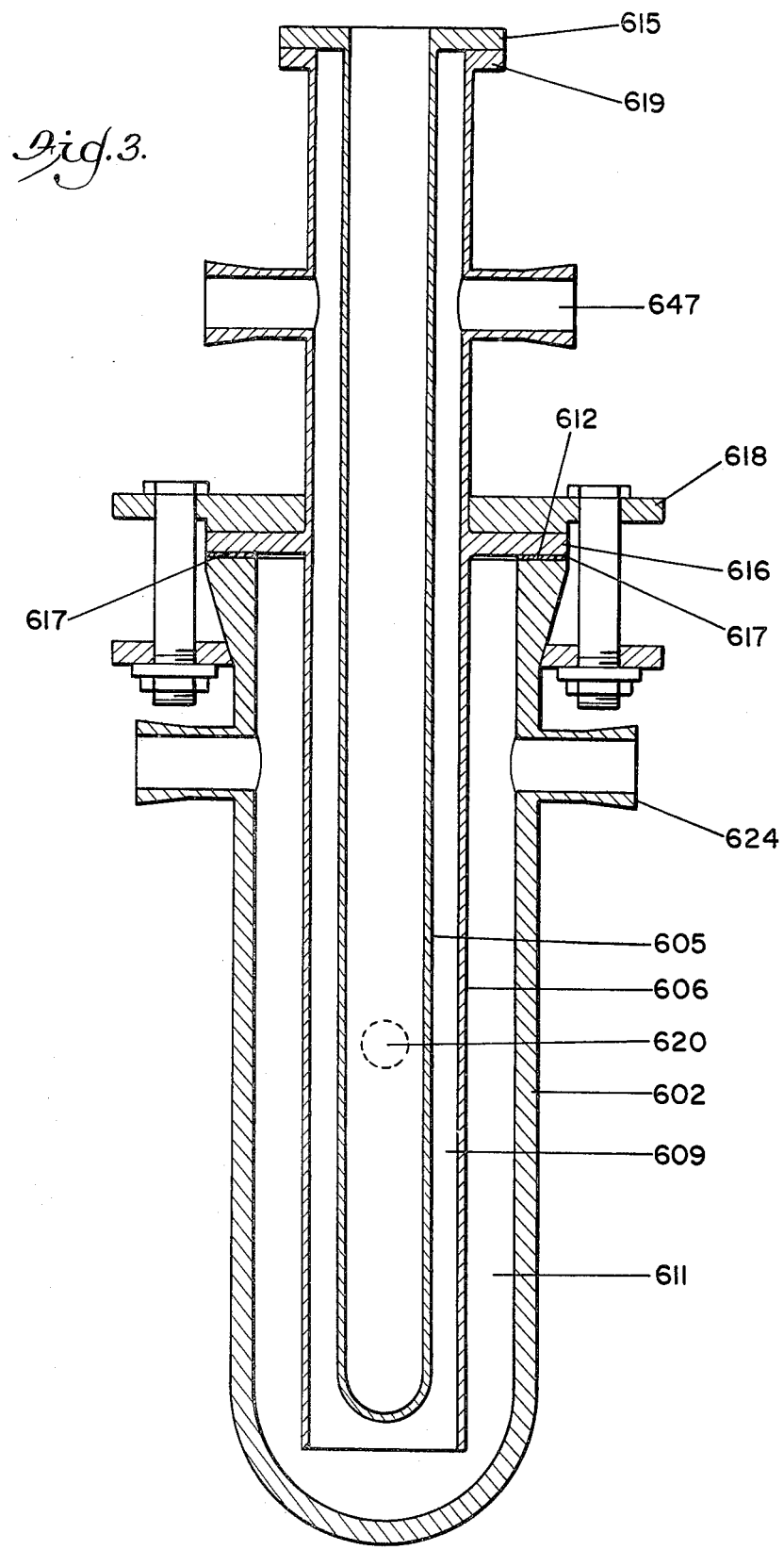
FIG. 3 is a longitudinal section of a third embodiment of the multichamber photoreactor according to the invention.
Figure 4:
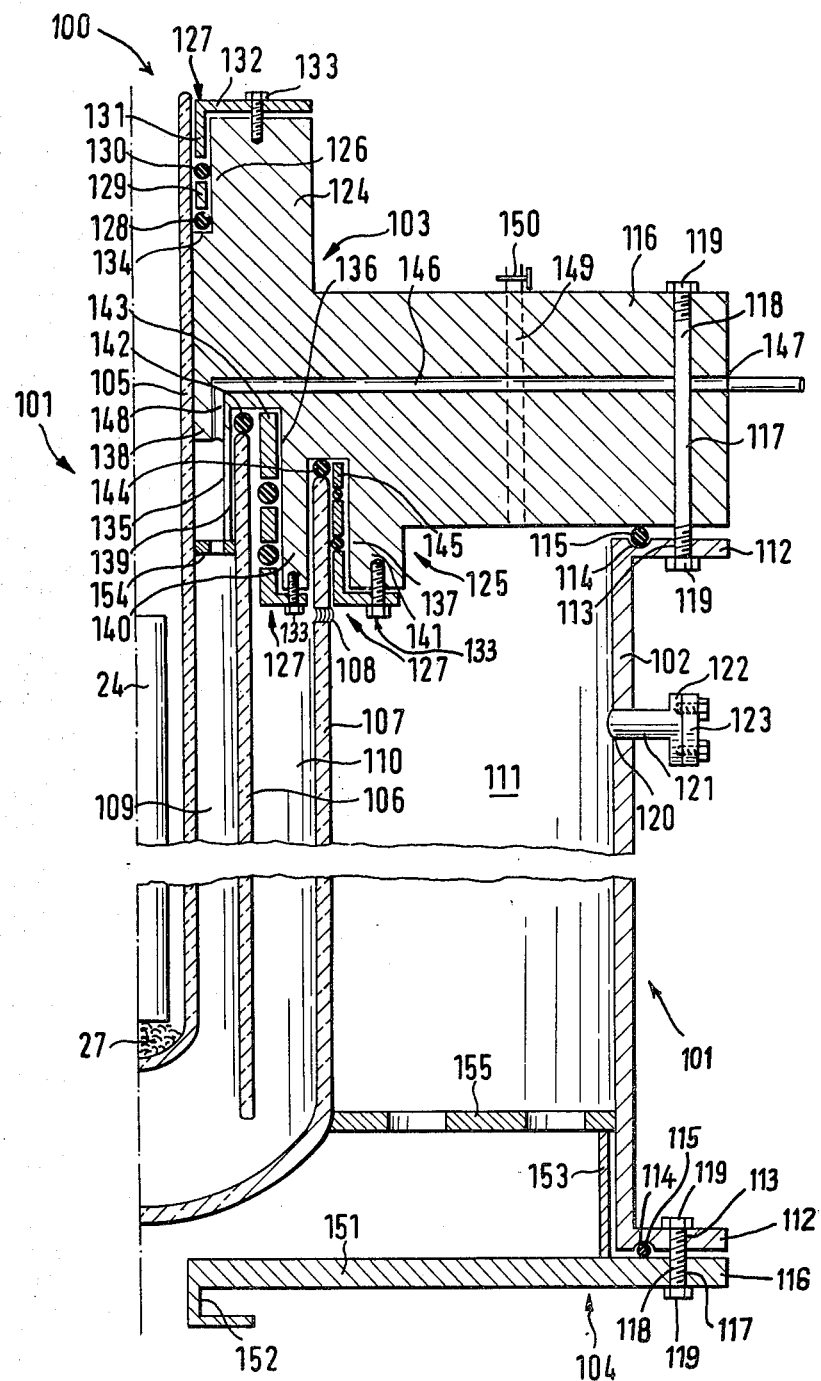
FIG. 4 is a longitudinal section of a portion of a fourth embodiment of the multichamber photoreactor according to the invention.

Multichamber photoreactors with annular respective arrangements of radiation source and flow reactor may be constructed from a number of silica tube sections which are placed inside each other according to their increasing diameters with the diameters selected so as to enable coaxial irradiation chambers of the respectively desired depths to be formed. Such silica glass tubes can be manufactured to the required precision in their dimensions and are commercially available with appropriate diameters and wall thicknesses. The silica glass tubes are centered relative to each other and then retained by closure members closing the flow reactor at the end faces thereof (see further below). The closure members have grooves sealable for instance by packing glands within which the silica glass tubes are retained. They are provided with internal passages and connections for effecting supply and discharge of the medium in parallel or series connection of the chambers. FIGS. 2 to 4 will show specific embodiments of annular multichamber photoreactors having an interior radiation source.

FIG. 2 shows such a two chamber photoreactor 200. Flow reactor 200 includes a housing formed by an exterior casing 202 opaque to the radiation, a first closure member 203, a second closure member 204 and a transparent interior envelope tube 205 retained at both closure members 203, 204. Interior envelope tube 205 is an open-ended silica glass tube. The flow reactor 200 is subdivided into two irradiation chambers 209, 211 by means of an intermediate silica glass tube 207 retained in closure members 203, 204 at both its ends. Tube 207 forms a window between chambers 209, 211 through which ultraviolet radiation may pass.

For connection to closure members 203, 204 exterior casing 202 has annular flanges 212 at both its ends. The flanges have bores 213 distributed adjacent their periphery. At the end faces of annular flanges 212 there are recesses 214 to receive sealing O-rings 215. Closure members 203, 204 include flanges 216 and 228 with bores 217 distributed adjacent their periphery. Exterior casing 202 and closure members 203, 204 are firmly and sealingly interconnected by bolts 218 extending through bores 213, 217 and secured by nuts 219.

Exterior casing 202 has, for purposes of observation and control, an observation port formed by an opening 220 within which is mounted a tube 221 carrying an annular flange 222 and a cover 223. Cover 223 may be silica glass when the port is used for observation purposes. Exterior casing 202 has a lateral connection 224 in a part thereof adjacent to closure member 203. Exterior casing 202, closure members 203, 204 and tubes 205, 207 are made of the same material as the corresponding components in three-chamber photoreactor 100.

Closure members 203, 204 are of generally annular design, the internal diameter being closely adapted to the outer diameter of envelope tube 205. Closure member 203 has an axial portion 225 extending from the interior periphery of flange 216 into the interior space of flow reactor 200 and serving to retain envelope tube 205 and silica glass tube 207 at one end of the flow reactor. From its outer face closure member 203 is provided with a counter bore 226 into which a packing gland 127 is inserted and is secured to the outside of closure member 203 by screws 133. The packing gland firmly and sealingly holds envelope tube 205. At the interior end axial portion 225 is provided with an annular groove 235 defined radially externally by an annular web 237. The outer diameter of axial portion 225 is closely adapted to the internal diameter of silica glass tube 207 so that one end thereof is slipped over the same. A sealing collar 240 held by tube or hose clamps (not shown) surrounds the free part of axial portion 225 and the end of silica glass tube 207. Thus the respective end of silica glass tube 207 will be firmly and sealingly retained at closure member 203.

Closure member 203 has a passage 246 ending in connection 247. At its interior end passage 246 connects with an axial passage 248 extending through axial portion 225 and opening into the base of annular groove 235. Thus communication is provided between connection 247 and interior irradiation chamber 209.

Closure member 204 has an axial portion 265 extending from the interior periphery of flange 228 at the side thereof remote from flow reactor 200. This axial portion serves to retain envelope tube 205 at the other end of flow reactor 200. In its outer face closure member 204 has a counterbore 266 into which a packing gland 127 is inserted. The packing gland is secured to the outside of closure member 204 by screws 133. The gland firmly and sealingly holds envelope tube 205 at this respective end of flow reactor 200. At the inner face of closure member 204 a ring 268 is secured by screws 267. Spring blades 269 project from said ring 268 in a crown-like arrangement and are arched externally to guide a protective cover 270 surrounding the adjacent end of silica glass tubes 207. Closure member 204 has an axially extending drain passage 249 connecting the exterior irradiation chamber 211 to a drain valve 250 at the outside of flange 228.

The flow between connections 224 and 247 through two chamber photoreactor 200 passes through irradiation chambers 209 and 211 communicating through the intermediate spaces between the spring blades 269 and corresponding gaps in cover 270. To generate a uniform flow pattern perforated plates 254, 255 like those in three chamber photoreactor 100 are provided. Perforated plate 254 is secured to web 237 of closure member 203 and acts upon the flow passing through the interior irradiation chamber 209. Perforated plate 255 abuts a ring 251 secured to the interior wall of exterior casing 202 which ring may also be formed integrally therewith; and at the inside, the plate 255 engages the end face of sealing collar 240. Retaining rings 256 secure perforated plate 255 against displacement. Plate 255 acts upon the flow passing through exterior irradiation chamber 211.

As described before with reference to two chamber photoreactor 1 traversed by parallel radiation the flow-dose rate of two chamber photoreactor 200 traversed by radially outwardly directed radiation is correspondingly composed from contributions originating in each one of both the irradiation chambers 209 and 211, too. As explained initially, exact derivation for the maximum flow-dose rate is complex. Therefore, the following presentation will be based on the initially mentioned approximation.

Without going into the details, it results also for two chamber photoreactor 200 that the maximum flow-dose rate within a limited range will depend only little on the depth $d_1$ and, respectively, on variations in the UV transmission of the medium.

It is of significance particularly in the field of water disinfection that different objects are to be achieved in practice frequently related to an upper or lower limiting value of the water UV transmission. Correspondingly the following Table 3 will show optimum values of the total depth $d_1+d_2$ and the depth $d_1$ of irradiation chamber 209 as a function of the UV transmission T (1 cm) of the medium for two kinds of design of two chamber photoreactor 200. Design (a) is for a two chamber photoreactor 200 adapted to media varying to lower values in their UV transmission while design (b) is adapted to media varying to higher values in their transmission.

TABLE 3

Depths $d_1$ and $d_1+d_2$ of optimized two chamber photoreactors 200 for media having UV transmissions in the range of T (1 cm) 0.4 to 0.9 and variable more to lower values sub (a) and more to higher values sub (b)

| (a) $T_1 \cdot T_2 = 0.34$; $d_1 + d_2 = \dfrac{-1.075}{\ln T (1\ cm)}$ ; $d_1 = \dfrac{-0.385}{\ln T (1\ cm)}$ | | | |
|---|---|---|---|
| $d_1 + d_2$ cm | T (1 cm) | $-\ln$ T (1 cm) | $d_1$ cm |
| 10.2 | 0.9 | 0.015 | 3.654 |
| 6.615 | 0.85 | 0.163 | 2.37 |
| 4.818 | 0.8 | 0.223 | 1.725 |
| 3.737 | 0.75 | 0.288 | 1.34 |
| 3.014 | 0.7 | 0.357 | 1.08 |
| 2.495 | 0.65 | 0.431 | 0.89 |
| 2.104 | 0.6 | 0.511 | 0.75 |
| 1.173 | 0.4 | 0.916 | 0.42 |

| (b) $T_1 \cdot T_2 = 0.25$; $d_1 + d_2 = \dfrac{-1.376}{\ln T (1\ cm)}$ ; $d_1 = \dfrac{-0.528}{\ln T (1\ cm)}$ | | | |
|---|---|---|---|
| $d_1 + d_2$ cm | T (1 cm) | $-\ln$ T (1 cm) | $d_1$ cm |
| 13.031 | 0.9 | 0.105 | 5.011 |
| 8.448 | 0.85 | 0.163 | 3.25 |
| 6.153 | 0.8 | 0.223 | 2.366 |
| 4.773 | 0.75 | 0.288 | 1.835 |
| 3.849 | 0.7 | 0.357 | 1.480 |
| 3.187 | 0.65 | 0.431 | 1.226 |
| 2.688 | 0.6 | 0.511 | 1.034 |
| 1.498 | 0.4 | 0.916 | 0.576 |
| 0.855 | 0.2 | 1.609 | 0.328 |

A further design of an annular two chamber photoreactor is presented in FIG. 3. The two chamber photoreactor 600 shown therein is also designed coaxially in accordance with the immersion type principle.

A container 602 made of Rotosil but which may also be made of glass or another material impermeable for UV radiation is open at the top and provided with a rounded bottom. At the open end it has a planely ground front face 612 and a circumferentially reinforced external wall in this range. Below the open end there are two diametrically opposed lateral connections 624. An interior envelope tube 605 terminating short of the rounded bottom is closed within the container 602 and serves to receive the UV radiation source (not shown); in the range of the source the envelope tube 605 is made of quartz glass or another material transparent to UV radiation and it is provided with an elongation made of Rotosil or another suitable material impermeable for the radiation. The envelope tube 605 is surrounded by a partition tube 606 made of quartz glass or another UV transparent material so that an irradiation chamber 609 immediately adjacent to the radiation source and a further irradiation chamber 611 are formed in container 602. In the range of the UV radiation source the container 602 is provided with a monitoring device 620 made of UV transparent material which may comprise a plate of quartz glass fused with Rotosil container 602.

Partition tube 606 is provided with an annular flange 616 of Rotosil welded thereto. The abutting face of the annular flange 616 facing the front face 612 of container 602 is ground flat and abuts the front face 612 through a gasket 617 made of poly tetrafluoroethylene. Container 602 is sealingly closed by means of an annular collar 618 (Schott & Gen., Mainz, Federal Republic of Germany) engaging the annular flange 616 and the reinforced end of container 602. Above annular flange 616 partition tube 606 carries two diametrically opposed lateral connections 647. At the end the partition tube 606 is provided with a flange ring 619 made of Rotosil and fused to a corresponding flange ring 615 at the exterior end of envelope tube 605 whereby the irradiation chamber 609 is sealingly closed.

The envelope tube 605 has an outer diameter $D_i = 4.6$ cm and a radius $r_i = 2.3$ cm, respectively; the partition tube 606 has an inner diameter of 7.6 cm and a wall thickness of 0.3 cm; the container 602 has an inner diameter of 12.1 cm. Thus the irradiation chamber 609 has a deth $d_1 = 1.5$ cm and the irradiation chamber 611 a depth $d_2 = 2.1$ cm. Two chamber photoreactor 600, accounting for the UV transmission of partition tube 606, is designed for a medium having a UV transmission T (1 cm) = 0.7 and varying more to higher UV transmission values in accordance with Table 3b) and for a medium having a UV transmission T (1 cm) = 0.75 and varying more to lower UV transmission values in accordance with Table 3a), respectively. Table 4 shows the variation in the flow-dose rate Q-40 (100 watts UV radiation at the face of incidence formed by envelope tube 605) as a function of the depth $d_1$ of irradiation chamber 609 at a constant total depth $d_1+d_2=3.6$ cm, neglecting the UV transmission of partition tube 606. A broad maximum of 12.3 m³/h will be recognized about the depths as selected. Over the entire range the linear rate of flow in irradiation chamber 609 will have favourable values greater than 0.1 to 0.3 m/s. Also, the radiation dose effective in irradiation chamber 609 and the total effective radiation dose at a flow rate of 5 m³/h are entered into the table; the total effective maximum will be found at the selected depths of $d_1=1.5$ cm and $d_1+d_2=2.1$ cm.

TABLE 4

Variable depths $d_1$, $d_2$; UV radiation dose (flow rate 5 m³/h) in irradiation chamber 609, in irradiation chambers 609, 611 and UV transmission $T_1$, $T_2$ therein, Q-40 (m³/h) and rate of flow $v_1$ in irradiation chamber 609 in a two chamber reactor 600 optimized for a medium having T (1 cm) = 0.7.

100 watts UV radiation; $r_i = 2.3$ cm; tube 606 wall thickness 0.3 cm; $d_1 + d_2 = 3.6$ cm; $T_1 \cdot T_2 = 0.354$.

| $d_1$ cm | $d_2$ cm | UV dose at flow rate 5 m³/h | | | | Q-40 (m³/h) 2-ch. | $v_1$ m/s |
|---|---|---|---|---|---|---|---|
| | | 2-ch. mWs/cm² | 1-chm. mWs/cm² | $T_1$ | $T_2$ | | |
| 0.1 | 3.5 | 67.8 | 6.9 | 0.972 | 0.365 | 8.5 | 15.955 |
| 0.2 | 3.4 | 73.0 | 13.0 | 0.944 | 0.376 | 9.1 | 8.401 |
| 0.3 | 3.3 | 77.5 | 18.7 | 0.917 | 0.387 | 9.7 | 5.825 |
| 0.4 | 3.2 | 81.4 | 23.8 | 0.891 | 0.398 | 10.2 | 4.499 |
| 0.5 | 3.1 | 84.8 | 28.4 | 0.866 | 0.410 | 10.6 | 3.678 |
| 0.6 | 3.0 | 87.8 | 32.6 | 0.841 | 0.422 | 11.0 | 3.111 |
| 0.7 | 2.9 | 90.4 | 36.4 | 0.818 | 0.434 | 11.3 | 2.692 |
| 0.8 | 2.8 | 92.5 | 39.9 | 0.794 | 0.447 | 11.6 | 2.366 |
| 0.9 | 2.7 | 94.3 | 43.0 | 0.772 | 0.460 | 11.8 | 2.105 |
| 1.0 | 2.6 | 95.7 | 45.8 | 0.75 | 0.473 | 12.0 | 1.889 |
| 1.1 | 2.5 | 96.8 | 48.4 | 0.729 | 0.487 | 12.1 | 1.707 |
| 1.2 | 2.4 | 97.7 | 50.7 | 0.708 | 0.501 | 12.2 | 1.551 |
| 1.3 | 2.3 | 98.3 | 52.8 | 0.688 | 0.516 | 12.3 | 1.416 |
| 1.4 | 2.2 | 98.6 | 54.6 | 0.668 | 0.531 | 12.3 | 1.297 |
| 1.5 | 2.1 | 98.7 | 56.3 | 0.65 | 0.547 | 12.3 | 1.192 |
| 1.6 | 2.0 | 98.5 | 57.8 | 0.631 | 0.562 | 12.3 | 1.098 |
| 1.7 | 1.9 | 98.2 | 59.1 | 0.613 | 0.579 | 12.3 | 1.013 |
| 1.8 | 1.8 | 97.6 | 60.3 | 0.596 | 0.596 | 12.2 | 0.937 |
| 1.9 | 1.7 | 96.2 | 61.3 | 0.579 | 0.613 | 12.1 | 0.867 |
| 2.0 | 1.6 | 96.0 | 62.2 | 0.562 | 0.631 | 12.0 | 0.804 |
| 2.1 | 1.5 | 94.9 | 62.9 | 0.547 | 0.65 | 11.9 | 0.746 |
| 2.2 | 1.4 | 93.7 | 63.6 | 0.531 | 0.668 | 11.7 | 0.692 |
| 2.3 | 1.3 | 92.3 | 64.1 | 0.516 | 0.688 | 11.5 | 0.643 |
| 2.4 | 1.2 | 90.8 | 64.5 | 0.501 | 0.708 | 11.4 | 0.598 |
| 2.6 | 1.0 | 87.4 | 65.1 | 0.473 | 0.75 | 10.9 | 0.516 |
| 2.8 | 0.8 | 83.5 | 65.4 | 0.447 | 0.794 | 10.4 | 0.446 |
| 3.0 | 0.6 | 79.2 | 65.3 | 0.422 | 0.841 | 9.9 | 0.384 |
| 3.2 | 0.4 | 74.5 | 65.1 | 0.398 | 0.891 | 9.3 | 0.330 |
| 3.3 | 0.3 | 72.0 | 64.9 | 0.387 | 0.917 | 9.0 | 0.305 |
| 3.4 | 0.2 | 69.4 | 64.6 | 0.376 | 0.944 | 8.7 | 0.282 |

Table 5 illustrates the range of adaptation for two chamber photoreactor 600 and presents the following data as a function of the UV transmission of the medium: In columns 2 and 3 the UV radiation dose effective at a rate of flow of 5 m³/h altogether and in irradiation chamber 609, respectively; in columns 4 and 5 the UV transmission in irradiation chamber 609 and the over-all UV transmission, respectively; in column 6 the flow-dose rate Q-40 in m³/h; in column 7 the linear flow rate in irradiation chamber 609. As will result from the table, two chamber photoreactor 600 as designed for media having a UV transmission of T (1 cm) = 0.7 will yield the considerable flow-dose rate 5.1 m³/h at the minimum dose of 40 milliwatt seconds per cm² even for a medium having a UV transmission of T (1 cm) = 0.5 at the sufficiently high rate of flow $v_1 = 0.49$ m/s in irradiation chamber 609.

TABLE 5

UV radiation doses in irradiation chamber 609, in irradiation chambers 609, 611 and UV transmissions $T_1$ and $T_1 \cdot T_2$ therein, Q-40 (m³/h) and rate of flow $v_1$ in irradiation chamber 609 of the two chamber photoreactor 600 optimized for a medium hving a UV transmission of T (1 cm) = 0.75 for different UV transmissions of the medium.

100 watts UV radiation; $r_i = 2.3$ cm; tube 606 wall thickness 0.3 cm; $d_1 = 1.5$ cm; $d_2 = 2.1$ cm.

| T(cm) | UV dose at flow rate 5 m³/h | | | | Q-40 | |
|---|---|---|---|---|---|---|
| | 2-ch. mWs/cm² | 1-ch. mWs/cm² | $T_1$ | $T_1 \cdot T_2$ | m³/h 2 ch. | $v_1$ m/s |
| 1.0 | 206.0 | 86.7 | 1.0 | 1.0 | 25.8 | 2.49 |
| 0.95 | 179.5 | 80.3 | 0.926 | 0.831 | 22.4 | 2.17 |
| 0.9 | 155.7 | 74.0 | 0.854 | 0.684 | 19.5 | 1.88 |
| 0.85 | 134.4 | 67.9 | 0.784 | 0.557 | 16.8 | 1.62 |
| 0.8 | 115.5 | 62.0 | 0.716 | 0.448 | 14.4 | 1.40 |
| 0.75 | 98.7 | 56.3 | 0.65 | 0.355 | 12.3 | 1.19 |
| 0.7 | 83.8 | 50.8 | 0.586 | 0.277 | 10.5 | 1.01 |
| 0.65 | 70.7 | 45.4 | 0.524 | 0.212 | 8.8 | 0.85 |
| 0.6 | 59.3 | 40.3 | 0.465 | 0.159 | 7.4 | 0.72 |
| 0.55 | 49.2 | 35.4 | 0.408 | 0.116 | 6.2 | 0.6 |
| 0.5 | 40.5 | 30.6 | 0.354 | 0.082 | 5.1 | 0.49 |

According to table 5 the two chamber photoreactor 600 yields high flow-dose rates for media having UV transmissions in the range of T (1 cm) 0.5 to 1.0. Particularly in combination with UV radiation sources having radiative powers equal to or greater than 1 watt per cm arc length (medium pressure mercury lamps having arc lengths of 20 or 30 cm; antimony doped Xenon high pressure lamps; Original Hanau Quarzlampen-GmbH; special low pressure mercury lamps; Grätzel, both companies in the Federal Republic of Germany) compact high-power photoreactors are obtained at reasonable costs and may be utilized for media of highly variable UV transmission. The high rates of flow in irradiation chamber 609 immediately adjacent to the radiation source offer high safety from operational troubles even if the composition of the medium to be irradiated changes relatively strongly. Corresponding cases of use are emergency water supply plants which may be operated by emergency power supplies. With the high power radiation source as mentioned above flow-dose rates Q-40 in the range of 15 to 20 m³/h will be obtained sufficient for the emergency water supply of 1500 people. In maritime disinfection plants, in pisciculture plants including water recirculation and for shell-fish purification such compact photoreactors are particularly useful due to their adaptability to wide ranges of UV transmission in the water to be irradiated. In combination with a lower-powered low pressure mercury lamp the two chamber photoreactors 600 are suitable for the independent disinfection of spring water or well water.

On the other hand, in combination with the high-powered radiation sources a lower rate of flow of the medium will be obtained at very much higher minimum doses, for example a rate of flow of 2 m³/h at a minimum dose of 100 milliwatt seconds per cm² for a medium having a UV transmission of T (1 cm) = 0.75. Such high minimum doses at the indicated consumption are required in the pharmaceutical and cosmetics, but also in the electronics industry.

At a predetermined maximum rate of flow in m/s the maximum flow rate through multichamber photoreactors is limited by the smallest respective chamber cross-section or, respectively, at equal lengths by the smallest chamber volume. Usually the dimension of the innermost chamber will have such a limiting function since the chamber cross-sections will rapidly increase with increasing distance from the center or axis, respectively, if equal chamber depths are provided.

A two chamber photoreactor of 100 cm length and optimized for a medium having a UV transmission of T (1 cm)=0.9 in accordance with table 6a) has the depths $d_1=3.7$ cm, $d_2=6.5$ cm, and $d_1+d_2=10.2$ cm. With an envelope tube radius $r_i=2.3$ cm the radiation doses effective in both the irradiation chambers will be related to each other like the volumes or, respectively, the cross-sectional areas of the irradiation chambers. The relatively small changes in flow-dose rate on varying the depth $d_1$ at constant over-all depth in the range of the maximum enables the volumes of both the chambers to be equalized without a substantial deterioration in the flow-dose rate. This will obtain at $d_1=4.0$ cm and $d_2=6.2$ cm, Q-40 decreasing only from the optimum value of 25.91 m$^3$/h to 25.22 m$^3$/h. In combination with the high-powered radiation sources as mentioned before the high rates of flow at throughputs up to 60 m$^3$/h are achieved more readily due to lower flow resistance.

Within the framework of the predetermined limits in overall thickness for two chamber photoreactors the depth ratios may be widely adapted to the respective rate of flow requirements at higher or lower throughputs, the flow-dose rate always being substantially above that achievable with single chamber photoreactors. One half of a three chamber photoreactor 100 designed for irradiation from its interior is illustrated in longitudinal section in FIG. 4. A lamp 24 of the aforementioned kind is included therein and may be singly or multiply reversed on itself to obtain increased radiation intensity. Lamp 24 is disposed in the interior of a flow reactor 101 near the axis thereof. The flow reactor includes a housing formed by an exterior casing 102 opaque to the radiation, a first closure member, generally 103, and a second closure member, generally 104. Within the housing is an interior, intermediate tube 105 transparent to the radiation and held by first closure member 103. Interior envelope tube 105 is a silica glass tube closed at one end at which end lamp 24 rests on a glass wool packing 27. Flow reactor 101 is subdivided into three irradiation chambers 109, 110, 111 by silica glass tubes 106 and 107. Tubes 106 and 107 form windows through which the ultraviolet radiation may pass. Silica glass tube 107 is closed at one end and provided with passage openings 108 in the wall near its open end. Both tubes 106 and 107 are held by first closure member 103.

Exterior casing 102 is provided with annular flanges 112 having bores 113 spaced adjacent their periphery for connection to closure members 103, 104 at the respective ends. The end faces of annular flanges 112 have recesses 114 to receive sealing O-rings 115. Closure members 103, 104 include flanges 116 having bores 117 spaced adjacent their periphery corresponding in number and diameter to bores 113 in annular flanges 112. Exterior casing 102 and closure members 103, 104 are arranged with their annular flanges 112 and 116 such that bores 113 and 117 are aligned to each other so that said members can become firmly interconnected by threaded bolts 118 extending through bores 113 and 117 and by nuts 119.

For purposes of observation and monitoring exterior casing 102 has an observation port in the region of the field of radiation emitted by lamp 24 and formed by an opening 120 into which a tube 121 having an outer annular flange 122 is secured. During non-use tube 121 is closed by a cover 123 firmly and sealingly, for instance by screwing, connected to annular flange 122. During use tube 121 is connected through a silica window (which may be cover 123) to the photodetector of an equipment for monitoring the radiation passing through the entire depth of flow reactor 101. To utilize the ultraviolet output impinging on the interior wall of exterior casing 102 in the irradiation of media having high transmission said interior wall may be provided with material reflective for ultraviolet rays. If an exterior casing of silica glass is employed, the reflective surface may also be located on the exterior wall of the casing to avoid te reflectivity to become affected by the medium.

Exterior casing 102 and closure members 103, 104 are made of metal like stainless steel, of metals having a protective coating like glass, enamel, plastic, of zinced iron sheet material, of ceramic; or any material having the appropriate mechanical strength which is resistant against ultraviolet radiation and does not give off foreign matter or noxious contaminants to the medium flowing therethrough will be applicable. To increase the mechanical strength and to facilitate processing and handling of envelope tube 105 and silica tubes 106, 107 said tubes may be fused to extensions for instance of vitreous silica positioned outside the radiation field as emitted by lamp 24.

Closure member 103 is generally of annular configuration and has an internal diameter closely adapted to the external diameter of envelope tube 105. The annular closure member 103 has two axial portions 124, 125 each projecting from a face of flange 116 and serving to retain envelope tube 105 and silica glass tubes 106, 107. First portion 124 is provided with a counterbore 126 at its outer end into which a packing gland 127 is inserted. Packing gland 127 comprises two O-rings 128, 130 separated by a guiding bush 129 and pressed against a step 134 formed at the interior end of counterbore 126 by means of a compression sleeve 131. Sleeve 131 includes an annular flange 132 which is secured to the outer face of first axial portion 124 by screws 133. Thus envelope tube 105 will be firmly and sealingly retained at the first axial portion 124. Second axial portion 125 is provided with three concentric annular grooves 135, 136, 137 each extending axially from the inside of flow reactor 101 and their depth decreasing radially from the interior to the exterior and separated by annular webs 138, 139, 140 and 141. Webs 138 and 139 have small and different axial heights and define the radially innermost annular groove 135 of greater depth. Radially intermediate annular groove 136 is defined by web 139 and web 140 of greater axial height while radially outermost annular groove 137 of smallest depth is enclosed between two webs 140, 141 of equal axial heights. Intermediate annular groove 136 serves to accommodate a first end of silica glass tube 106 which abuts the base of annular groove 136 with the interposition of an O-ring 142, a bushing 143 enclosing O-ring 142 and said first end of silica glass tube 106. Tube 106 is retained firmly and sealingly within intermediate annular groove 136 by a packing gland 127 secured to the outer face of web 140 by screws. The outermost annular groove 137 serves to accommodate silica glass tube 107 closed at one end. The open end of tube 107 abuts the base of annular groove 137 with the interposition of an O-ring 144. A bushing 145 encloses O-ring 144 and said open end of silica glass tube 107. Tube 107 is firmly and sealingly retained within outermost annular groove 137 above passage openings 108 by a packing gland 127 secured to the outer face of web 141 by screws.

Closure member 103 has two radial passages 146 ending at diametrically opposed positions in connections 147 for conduits at the circumferential surface of flange 116. Both radial passages 146 are connected each at the interior end with a respective axial passage 148 opening into the base of annular groove 135. Thus communication is provided between connections 147 and the internal irradiation chamber 109. Additionally, flange 116 has a vent passage 149 extending axially therethrough and connecting the exterior irradiation chamber 111 to a venting valve 150 located at the outer face of flange 116.

Closure member 104 comprises a plate 151 having a central connection 152. A ring 153 is engaged to the interior face of plate 151 and peripherally abuts the interior wall of exterior casing 102.

Flow is conducted through three-chamber photoreactor 100 between connections 147 and 152 through irradiation chambers 109, 110, and 111. Irradiation chambers 110 and 111 communicate with each other through the passage openings 108 in the wall of silica glass tube 107 closed at one end. To generate a uniform flow pattern annular perforated plates 154, 155 are provided. Perforated plate 154 is secured to web 139 of first closure member 103 and affects the flow passing through interior irradiation chamber 109. Perforated plate 155 engages ring 153 which engages the interior face of plate 151 of second closure member 104 and affects the flow passing through exterior irradiation chamber 111. Silica glass tube 107 abuts the interior edge of plate 155 and thus is additionally guided at the closed end thereof. Perforated plates 154, 155 are made of a material resistant to ultraviolet radiation and to the medium flowing therethrough and which does not give off any foreign matter or noxious contaminants to the medium. Such material might be stainless steel, coated metal, plastic, ceramic, silica, or glass. The width of the perforation is such as to not substantially impair the flow but to generate uniform flow pattern across the passage area. For that purpose the holes forming the perforation may be substituted with appropriate, differently shaped openings.

For continuous operation the direction of flow through flow reactor 101 is hardly significant. Substantial differences, however, may exist at the start of the operation. With repeatedly interrupted operation it may be desirable to obtain a medium of the required degree of purification or disinfection even within very short periods of time after start. In that case it will be expedient to have the medium flow from connection 152 and the exterior irradiation chamber 111 through the interior irradiation chamber 109 to connections 147. With the same direction of flow it will be achieved in cases of deposit formation that interfering effects are restricted to the exterior irradiation chambers without rapidly calling the entire result into question. For the reason of lamp cooling, and also in cases in which gases are introduced, a direction of flow from the interior to the exterior will be preferred in general.

The three chamber photoreactor 100 as shown in FIG. 4 constitutes a combination of a two chamber photoreactor optimized with respect to flow-dose rate with an additional irradiation chamber 109 immediately adjacent to the radiation source in such a way that an optimum flow-dose rate is achieved. Table 6 shows the data for such combinations which according to tables 6(a) and 6(b) are adapted to media having UV transmissions varying to lower and higher values, respectively, in correspondence with tables 3(a) and 3(b).

TABLE 6

Depths $d_1$, $d_2$, $d_2+d_3$ of three chamber photoreactors 100 optimized for media having UV transmissions in the range of T (1 cm) 0.2 to 0.9 and adapted to variations (a) to lower, (b) to higher values.

| (a) $T_2 \cdot T_3 = 0.34$ $d_2 + d_3 = \frac{-1.075}{\ln T (1\,cm)}$ cm, $d_2 = \frac{-0.385}{\ln T (1\,cm)}$ cm, $d_1 = \frac{-0.328}{\ln T (1\,cm)}$ cm ||||
|---|---|---|---|
| $d_2 + d_3$ cm | T (1 cm) | $-\ln T$ (1 cm) | $d_2$ cm | $d_1$ cm |
| 10.2 | 0.9 | 0.105 | 3.654 | 3.113 |
| 6.615 | 0.85 | 0.163 | 2.37 | 2.02 |
| 5.588 | 0.825 | 0.192 | 2.001 | 1.705 |
| 4.818 | 0.8 | 0.223 | 1.725 | 1.47 |
| 3.737 | 0.75 | 0.288 | 1.34 | 1.14 |
| 3.014 | 0.7 | 0.357 | 1.08 | 0.92 |
| 2.495 | 0.65 | 0.431 | 0.89 | 0.761 |
| 2.104 | 0.6 | 0.511 | 0.75 | 0.642 |
| 1.173 | 0.4 | 0.916 | 0.42 | 0.358 |
| (b) $T_2 \cdot T_3 = 0.25$ $d_2 + d_3 = \frac{-1.376}{\ln T (1\,cm)}$ cm, $d_2 = \frac{-0.528}{\ln T (1\,cm)}$ cm, $d_1 = \frac{-0.446}{\ln T (1\,cm)}$ cm ||||
| $d_2 + d_3$ cm | T (1 cm) | $-\ln T$ (1 cm) | $d_2$ cm | $d_1$ cm |
| 13.031 | 0.9 | 0.105 | 5.011 | 4.233 |
| 8.448 | 0.85 | 0.163 | 3.25 | 2.744 |
| 6.153 | 0.8 | 0.223 | 2.366 | 1.999 |
| 4.773 | 0.75 | 0.288 | 1.835 | 1.550 |
| 3.849 | 0.7 | 0.357 | 1.480 | 1.25 |
| 3.187 | 0.65 | 0.431 | 1.226 | 1.035 |
| 2.688 | 0.6 | 0.511 | 1.034 | 0.873 |
| 1.498 | 0.4 | 0.916 | 0.576 | 0.487 |
| 0.855 | 0.2 | 1.609 | 0.328 | 0.277 |

The three chamber photoreactor may also be designed in reversed series such that a two chamber photoreactor optimized in terms of flow-dose rate for media having a UV transmission in the range of T (1 cm) 0.4 to 0.6 is combined with another irradiation chamber 111 of greater depth ($d_3 = 3.5$ cm) series connected with respect to the direction of radiation. Table 7 shows the radiation doses effective in irradiation chambers 109, 110, and 111 for media having UV transmissions in the range of T (1 cm) 0.2 to 0.9, as well as the UV transmission, the over-all flow-dose rate Q-40 and the flow-dose rate of the interior irradiation chambers 109 and 110 forming the two chamber photoreactor. It will be seen that such a three chamber photoreactor may be nearly universally utilized for water in the range of occurring UV transmissions. Thus in the range of low UV transmissions of the medium (T (1 cm) = 0.6 and below) only the two chamber photoreactor formed by irradiation chambers 109 and 110 will become effective practically, while at higher UV transmissions (T (1 cm) = 0.6 and above) the three chamber photoreactor with its considerably more favourable flow-dose rate will become increasingly effective. Such a far-reaching adaptation of a photoreactor to so much different UV transmissions is unachievable with two chamber photoreactors.

TABLE 7

Universal three chamber photoreactor: Flow-dose rate Q-40 and dose distribution at constant rate of flow Q=5 m$^3$/h; $r_1$=2.3 cm; $d_1$=0.75 cm; $d_2$=1.1 cm;

$d_3 = 3.5$ cm; $v_1(d_1) = 4.538$ m/s. 100 watts radiation radially directed into the medium

| | UV dose distribution at 5 m³/h | | | UV transmission | | Q-40 (m³/h) | |
|---|---|---|---|---|---|---|---|
| T (1 cm) | 3-ch. mWs/cm² | 2-ch.(1 + 2) mWs/cm² | 1-ch. (1) mWs/cm² | $T_1 \cdot T_2 \cdot T_3$ | $T_1 \cdot T_2$ | 3-ch. | 2-ch. |
| 0.95 | 236.8 | 100.8 | 45.6 | 0.764 | 0.914 | 29.6 | 12.6 |
| 0.9 | 196.4 | 94.0 | 43.8 | 0.575 | 0.832 | 24.6 | 11.8 |
| 0.85 | 163.2 | 87.4 | 41.9 | 0.426 | 0.752 | 20.4 | 10.9 |
| 0.8 | 136.1 | 81.0 | 40.1 | 0.310 | 0.677 | 17.0 | 10.1 |
| 0.75 | 114.0 | 74.7 | 38.2 | 0.221 | 0.604 | 14.3 | 9.3 |
| 0.7 | 96.0 | 68.6 | 36.2 | 0.154 | 0.536 | 12.0 | 8.6 |
| 0.65 | 81.3 | 62.7 | 34.3 | 0.104 | 0.471 | 10.2 | 7.8 |
| 0.6 | 69.2 | 57.0 | 32.3 | 0.068 | 0.409 | 8.65 | 7.13 |
| 0.55 | 59.2 | 51.5 | 30.2 | 0.043 | 0.351 | 7.4 | 6.4 |
| 0.5 | 50.8 | 46.1 | 28.2 | 0.0263 | 0.297 | 6.4 | 5.8 |
| 0.45 | 43.7 | 41.0 | 26.0 | 0.0151 | 0.247 | 5.5 | 5.1 |
| 0.4 | 37.4 | 36.0 | 23.8 | 0.0081 | 0.201 | 4.7 | 4.5 |
| 0.35 | 31.9 | 31.2 | 21.6 | 0.0040 | 0.159 | 4.0 | 3.9 |
| 0.3 | 26.9 | 26.5 | 19.2 | 0.0018 | 0.122 | 3.4 | 3.3 |
| 0.25 | 22.2 | 22.1 | 16.7 | 0.0007 | 0.088 | 2.8 | 2.8 |
| 0.2 | 17.8 | 17.8 | 14.2 | 0.0002 | 0.06 | 2.2 | 2.2 |

Annular three chamber photoreactor 100 as described before with reference to FIG. 4 and table 7 demonstrates one of the advantages of the multichamber principle, namely the optimum adaptation of a photoreactor to a wide range of different water properties. Additionally the multichamber principle offers specific advantages in the range of water meeting highest quality requirements as asked for in the electronics industry, in the pharmaceutical industry or in medicine (Aqua ad injectabilia). The properties of such water made available therefor generally by distillation, de-ionization, ultra-filtration, reverse osmosis or adsorption, respectively, exceed in respect of their UV transmission generally a transmission of T (1 cm)=0.9 considerably and should have transmissions above T (1 cm)=0.98 in the final product. Multichamber photoreactors optimized for UV transmissions in the range about T (1 cm)=0.9 are suited for water of the highest quality, too, although not optimized therefor in accordance with the formulas given before; however, optimization in regard of said highest purity water would result in technically difficult and expensive structures which, additionally, would have deteriorated throughflow properties. Adaptation of the photoreactor to an increase in the UV transmission of the water while being irradiated will be particularly desirable if oxidative removal of organic impurities is attained in addition to bactericidal action. Surprisingly it has now been found that a three chamber photoreactor optimized for a UV transmission of T (1 cm)=0.9 will retain the superiority in comparison to the single chamber reactors as predominantly used presently even in the range of highest purity water UV transmissions. This is also true for two chamber photoreactors correspondingly. In any case the superior adaptation to variable UV transmissions specifically in the field of highest purity water adds to the superior economy in the use of multichamber photoreactors for, by way of example, disinfection and photo-oxidative water purification.

In the foregoing the conditions have been illustrated for embodiments including UV radiation sources of relatively great length to clarify the relations basically. In practice, however, the actual length of the UV radiation sources will have to be accounted for. Emission of radiation therefrom does not occur as from a point source and also not from a line of point sources, but from different surfaces with point sources located thereon. Due to emission and irradiation occurring under different angles a profile of irradiation intensities will form in the medium under irradiation comprising increased absorption in the vicinity of the source. Accordingly, with increasing distance from the source the actual radiation intensity will be progressively lower than the calculated radiation intensity which effect will increase with decreasing UV transparency of the medium. In dimensioning multichamber photoreactors thus additional corrections have to be made for non-ideal radiation sources to adapt the reactor to the real radiation intensity profile within the medium, subdivision of the reactor and decrease in the depth $d_1$ being of advantage in this respect (S. M. Jacob, J. S. Dranoff, AIChE Journal, Vol. 16, No. 3 (1970) pages 359 to 363).

As described in the previous application, the aforementioned photoreactors can be readily used in combination with other equipment. So the photoreactors as described with reference to FIGS. 2 to 4 above may be readily combined with pressure balancing equipment as shown in FIG. 10 of the previous application and it will also be immediately evident that such photoreactors are readily incorporated into a recirculation system in accordance with FIGS. 13 to 15 of the previous application. Also, the rate of flow through the photoreactors as described before may be easily controlled by means of the control apparatus according to FIG. 15 in the previous application. Finally, the depth of the irradiation chamber formed around the envelope tubes inside a tank reactor according to FIGS. 2 to 8 in the previous application and the distance between the irradiation units located in such tank reactor may be readily selected so as to at least approximately realize the optimum conditions indicated above for annular two or three chamber photoreactors.

I claim:

1. An apparatus for purifying a fluid medium at a predetermined minimum radiation dose of ultraviolet radiation comprising a flow reactor defining an irradiation volume having two sides and through which volume said medium flows, at least one ultraviolet radiation source positioned to introduce ultraviolet radiation into the medium into said volume at least at one of said sides, and comprising further at a given location within said irradiation volume first means forming windows transparent to ultraviolet radiation and spaced from each other and second means defining one side of said irradiation volume, a total number n, less than four, of successive irradiation chambers and windows being provided through which the radiation will pass from one irradiation chamber to the next, said apparatus being characterized by the relationship between the irradiation intensity, the character of the medium and the depth of the medium in the irradiation chambers traversed by the radiation being established so that not more than fifty percent and not less than 5 percent of the radiation incident into the irradiation volume is absorbed by the medium in the first one of said successive irradiation chambers and substantially the remainder escapes into the immediately adjacent irradiation chamber, and so that the total radiation absorbed by the medium in all the irradiation chambers does not exceed $(1-0.5^n) \cdot 100$ percent of the radiation incident into the irradiation volume.

2. Apparatus as in claim 1 wherein for a medium having a UV transmission in the range of T (1 cm) 0.1 to 0.9 (1 cm cuvette; wavelength 254 nm) the relationship between the irradiation intensity, the UV transmission of the medium, and the depth of the medium in the irradiation chambers traversed by the radiation is established so that not more than 50 percent and not less than 20 percent of the incident radiation is absorbed by the medium in the irradiation chamber immediately adjacent to the irradiation source and substantially the remainder escapes to an irradiation chamber immediately adjacent said one irradiation chamber; and the total radiation absorbed by the medium in all the irradiation chambers does not exceed $(1-0.5^n) \cdot 100$ percent of the total incident radiation.

3. Apparatus as in claim 1 or claim 2 wherein two adjacent irradiation chambers traversed by substantially parallel UV radiation are provided and wherein for optimum efficiency in terms of flow-dose rate the relationship between the irradiation intensity, the UV transmission of the medium, and the depth of the medium in the irradiation chambers traversed by the radiation is established so that the decadic extinction by said medium in the irradiation chamber immediately adjacent to the irradiation source is about $E=0.275$ and the total decadic extinction by said medium in both said irradiation chambers is about $E=0.710$.

4. Apparatus as in claim 3 wherein for a medium having a UV transmission T (1 cm) 0.6 to 0.9 (1 cm cuvette; wavelength 254 nm) the depth of the medium traversed by the radiation is about 1.8 cm in the irradiation chamber immediately adjacent to the irradiation source and about 4.6 cm in the sum of both said irradiation chambers.

5. Apparatus as in claim 3 wherein for a medium having a UV transmission T (1 cm) 0.35 to 0.65 (1 cm cuvette; wavelength 254 nm) the depth of the medium traversed by the radiation is about 0.9 cm in the irradiation chamber immediately adjacent to the irradiation source and about 2.3 cm in the sum of both said irradiation chambers.

6. Apparatus as in claim 1 or claim 2 wherein two adjacent annular irradiation chambers traversed by substantially radially directed radiation and an irradiation source extending along their common axis are provided and wherein for optimum efficiency in terms of flow-dose rate the relationship between the irradiation intensity, the extinction by the medium and the depth of the medium traveresed by the radiation is established so that the decadic extinction by said medium in the irradiation chamber immediately adjacent to the irradiation source is in the range of $E=0.16$ to 0.25 and the total decadic extinction by the medium in the sum of both said irradiation chambers is in the range of $E=0.45$ to 0.65.

7. Apparatus as in claim 6 wherein for optimum efficiency in terms of flow-dose rate and for adaptation to a medium varying to lower values in its UV transmission the relationship between the irradiation intensity, the extinction by the medium and the depth of the medium traversed by the radiation is established so that the decadic extinction by said medium in the irradiation chamber immediately adjacent to the irradiation source is about $E=0.16$ and the total decadic extinction by the medium in the sum of both said irradiation chambers is about $E=0.47$.

8. Apparatus as in claim 6 wherein for optimum efficiency in terms of flow-dose rate and for adaptation to a medium varying to higher values in its UV transmission the relationship between the irradiation intensity, the extinction by the medium and the depth of the medium traversed by the radiation is established so that the decadic extinction by said medium in the irradiation chamber immediately adjacent to the irradiation source is about $E=0.23$ and the total decadic extinction by the medium in the sum of both said irradiation chambers is about 0.60.

9. Apparatus as in claim 6 wherein for optimum efficiency in terms of flow-dose rate and for adaptation to a medium having a UV transmission of T (1 cm) 0.75 (1 cm cuvette; wavelength 254 nm) the depth of the medium traversed by the radiation is about 1.5 cm in the irradiation chamber immediately adjacent to the irradiation source and the total depth is about 6.2 cm in the sum of both the irradiation chambers.

10. Apparatus as in claim 6 wherein the irradiation chamber immediately adjacent to the irradiation source is defined, on the one side, by an envelope tube closed at one end and receiving the irradiation source in an immersion-type arrangement and, on the other side, by a partition tube coaxially extending around said envelope tube and made of UV transparent material in the region of the length of the arc of said irradiation source and wherein said envelope tube and said partition tube are commonly and sealingly inserted into a container open at one end and made of material impermeable for the UV radiation, said container being provided with at least two lateral connections and with a monitoring device and being arranged coaxially with respect to said envelope tube and said partition tube to define together with the latter a second irradiation chamber.

11. Apparatus as in claim 10 wherein the container is made of rotosil and has a ground front face at the open end, wherein the partition tube has an annular flange planely ground and adapted to the front face on said container and at the end located outside of said container a flange for sealing connection to a correspondingly designed end of the envelope tube.

12. Apparatus as in claim 1 or claim 2 wherein three adjacent annular irradiation chambers traversed by substantially radially directed radiation and an irradiation source extending along their common axis are provided comprising two irradiation chambers of a configuration optimized in efficiency in terms of flow-dose rate and a third irradiation chamber to render optimum efficiency in terms of flow-dose rate for the entire apparatus.

13. Apparatus as in claim 12 wherein for optimum efficiency in terms of flow-dose rate for a medium having a UV transmission in the range of T (1 cm) 0.2 to 0.9 (1 cm cuvette; wavelength 254 nm) the relationship between the irradiation intensity, the extinction by the medium and the depth of the medium traversed by the radiation is established so that the decadic extinction by said medium in the irradiation chamber immediately adjacent to the irradiation source is in the range of $E=0.14$ to 0.20 and the total decadic extinction by the medium in the sum of the three irradiation chambers is in the range of $E=0.60$ to 0.80.

14. Apparatus as in claim 13 wherein for optimum efficiency in terms of flow-dose rate and for adaptation to a medium varying to lower values in its UV transmission the relationship between the irradiation intensity, the extinction by the medium and the depth of the medium traversed by the radiation is established so that the decadic extinction by said medium in the irradiation chamber immediately adjacent to the irradiation source is about $E=0.14$ and the total decadic extinction by the medium in the sum of the three irradiation chambers is about E 0.61.

15. Apparatus as in claim 13 wherein for optimum efficiency in terms of flow-dose rate and for adaptation to a medium varying to higher values in its UV transmission the relationship between the irradiation intensity, the extinction by the medium and the depth of the medium traversed by the radiation is established so that the decadic extinction by said medium in the irradiation chamber immediately adjacent to the irradiation source is about $E=0.19$ and the total decadic extinction by the medium in the sum of the three irradiation chambers is about $E=0.79$.

16. Apparatus as in claim 13 wherein for optimum efficiency in terms of flow-dose rate for a medium having a UV transmission in the ranges of T (1 cm) 0.1 to 0.9 (1 cm cuvette; wavelength 254 nm) two adjacent annular irradiation chambers of a configuration optimized in efficiency in terms of flow-dose rate for a medium having a UV transmission in the range of T (1 cm) 0.4 to 0.6 are provided and a third irradiation chamber surrounding the same externally to define a depth of the medium of 3.5 cm traversed by the radiation.

17. Apparatus as in claim 1 or claim 2 wherein a high-powered radiation source is used providing for preferably more than 0.5 watts of UV radiation in the effective wavelength range per centimeter of useful irradiation chamber length.

18. Apparatus as in claim 1 or claim 2 wherein the medium to be irradiated is exposed to a UV radiation dose of preferably at least 12 milliwatt seconds per square centimeter in the irradiation chamber immediately adjacent to the radiation source.

19. A process for purifying a fluid medium with a predetermined minimum radiation dose of ultraviolet radiation wherein, at a given location, a number n, less than four, of series connected flow paths to be passed consecutively by said medium are provided in juxtaposition to each other and the incident ultraviolet radiation is first introduced into one of said paths and permitted to escape from said path into other of said paths, in which process the relationship between the irradiation intensities effective in each one of said flow paths and the total rate of flow of the medium through all said flow paths is established so that the sum of the fractional doses applied to the medium being passed through each one of said series connected flow paths equals said predetermined minimum radiation dose applied to the medium when it has passed consecutively through all said flow paths, said process being characterized by:

two of the flow paths provided in juxtaposition to each other having a depth ratio in the range of about 0.34 to about 0.47, said depth ratio being defined by the depth of the smaller one of said two flow paths divided by the sum of the depths of said two flow paths, and the relationship between the irradiation intensity, the character of the medium and the sum of the depths of the medium in said two flow paths being established so that the total radiation absorbed by the medium in both said two flow paths does not exceed 90 percent of the incident radiation.

20. A process of purifying a fluid medium with a predetermined minimum radiation dose of ultraviolet radiation wherein, at a given location, a number n, less than four, of series connected flow paths to be passed consecutively by said medium are provided in juxtaposition to each other and the incident ultraviolet radiation is first introduced into one of said paths and permitted to escape from said one path into other of said paths, said process being characterized by:

the relationship between the irradiation intensity, the character of the medium and the depth of the medium traversed by the irradiation being established so that about 25 to about 50 percent of the incident radiation is absorbed by the medium in said one path and substantially the remainder escapes to a flow path immediately adjacent said one path;

the total radiation absorbed by the medium in all the flow paths is in the range of 60 to 85 percent of the total incident radiation; and the relationship between the irradiation intensities effective in each one of said flow paths and the total rate of flow of the medium through all said flow paths being established so that the sum of the fractional doses applied to the medium being passed through each one of the series connected flow paths equals the predetermined minimum radiation dose applied to the medium when it has passed consecutively through all said flow paths.

21. A process as in claim 20 wherein the number n of series connected flow paths is equal to two and the flow paths are traversed by substantially parallel UV radiation and wherein for optimum efficiency in terms of flow-dose rate the relationship between the irradiation intensity, the extinction by the medium and the depth of the medium traversed by the radiation is established so that the decadic extinction by said medium in the flow path immediately adjacent to the irradiation source is about $E=0.275$ and the total decadic extinction by said medium in both said flow paths is about $E=0.710$.

22. A process as in claim 21 wherein for a medium having a UV transmission in the range of T (1 cm) about 0.6 to about 0.9 (1 cm cuvette, wavelength 254 nm) the depth of the medium traversed by the radiation is about 1.8 cm in the flow path immediately adjacent to the irradiation source and about 4.6 cm in the sum of both said flow paths.

23. A process as in claim 21 wherein for a medium having a UV transmission in the range of T (1 cm) about 0.35 to about 0.75 (1 cm cuvette, wavelength 254 nm) the depth of the medium traversed by the radiation is about 0.9 cm in the flow path immediately adjacent to the irradiation source and about 2.3 cm in the sum of both said flow paths.

24. A process as in claim 20 wherein the number n of series connected flow paths is equal to two and the flow paths are of annular configuration and traversed by substantially radially directed UV radiation and wherein for optimum efficiency in terms of flow-dose rate the relationship between the irradiation intensity, the extinction by the medium and the depth of the medium traversed by the radiation is established so that the decadic extinction by said medium in the flow path immediately adjacent to the irradiation source is in the range of $E=0.16$ to 0.25 and the total decadic extinction by the medium in the sum of both said flow paths is in the range of $E=0.45$ to 0.65.

25. A process as in claim 24 wherein for optimum efficiency in terms of flow-dose rate and for adaptation to a medium varying to lower values in its UV transmission the relationship between the irradiation intensity, the extinction by the medium and the depth of the medium traversed by the radiation is established so that the decadic extinction by said medium in the flow path immediately adjacent to the irradiation source is about 0.16 and the total decadic extinction by the medium in the sum of both said flow paths is about 0.47.

26. A process as in claim 24 wherein for optimum efficiency in terms of flow-dose rate and for adaptation to a medium varying to higher values in its UV transmission the relationship between the irradiation intensity, the extinction by the medium and the depth of the medium traversed by the radiation is established so that the decadic extinction by said medium in the flow path immediately adjacent to the irradiation source is about 0.23 and the total decadic extinction by the medium in the sum of both said flow paths is about 0.60.

27. A process as in claim 24 wherein for optimum efficiency in terms of flow-dose rate in adaptation to a medium having a UV transmission of about T (1 cm) 0.75 (1 cm cuvette, wavelength 254 nm) the depth of the medium traversed by the radiation is about 1.5 cm in the flow path immediately adjacent to the irradiation source and the total depth is about 6.2 cm in the sum of both said flow paths.

28. A process as in claim 20 wherein the number n of series connected flow paths is equal to three and the flow paths are of annular configuration and traversed by substantially radially directed UV radiation and wherein for optimum efficiency in terms of flow-dose rate and for a medium having a UV transmission in the range of T (1 cm) 0.2 to 0.9 (1 cm cuvette, wavelength 254 nm) the relationship between the irradiation intensity, the extinction by the medium and the depth of the medium traversed by the radiation is established so that the decadic extinction by said medium in the flow path immediately adjacent to the irradiation source is in the range of $E=0.14$ to 0.20 and the total decadic extinction by the medium in all three said flow paths is in the range of $E=0.60$ to 0.80.

29. A process as in claim 28 wherein for optimum efficiency in terms of flow-dose rate and for adaptation to a medium varying to lower values in its UV transmission the relationship between the irradiation intensity, the extinction by the medium and the depth of the medium traversed by the radiation is established so that the decadic extinction by said medium in the flow path immediately adjacent to the irradiation source is about $E=0.14$ and the total decadic extinction by the medium in all three said flow paths is about $E=0.61$.

30. A process as in claim 28 wherein for optimum efficiency in terms of flow-dose rate and for adaptation to a medium varying to higher values in its UV transmission the relationship between the irradiation intensity, the extinction by the medium and the depth of the medium traversed by the radiation is established so that the decadic extinction by said medium in the flow path immediately adjacent to the irradiation source is about $E=0.19$ and the total decadic extinction by the medium in all three said flow paths is about $E=0.79$.

31. A process as in any one of claims 19 to 27 wherein the number n of series connected flow paths is equal to three and the flow paths are of annular configuration and wherein for optimum efficiency in terms of flow-dose rate for a medium having a UV transmission in the range of T (1 cm) 0.1 to 0.99 (1 cm cuvette; wavelength 254 nm) two adjacent flow paths of a configuration optimized in efficiency in terms of flow-dose rate for a medium having a UV transmission in the range of T (1 cm) 0.4 to 0.6 and surrounded externally by an adjacent third flow path having a depth of the medium traversed by the radiation of about 3.5 cm are provided.

32. A process as in claim 19 wherein for a medium having a UV transmission of T (1 cm) greater than 0.65, preferably greater than 0.75 (1 cm cuvette; wavelength 254 nm) the relationship between the irradiation intensity, the UV transmission of the medium and the depth of the medium traversed by the radiation is established so that not more than 50 percent and not less than 5 percent of the incident radiation is absorbed by said medium in the flow path immediately adjacent to the irradiation source and substantially the remainder escapes to a flow path immediately adjacent said one path; and the total radiation absorbed by the medium in all the flow paths is not less than 10 percent and not more than 85 percent of the total incident radiation.

33. A process of purifying a fluid medium having a UV transmission in the range of T (1 cm) 0.8 and greater (1 cm cuvette; wavelength 254 nm) as in any one of claims 19 to 30 wherein the relationship between the irradiation intensity, the character of the medium and the depth of the medium traversed by the irradiation is established so as to corresond to an optimum efficiency in terms of flow-dose rate in adaption to a medium having a UV transmission of T (1 cm) about 0.65, preferably 0.75.

34. A process of purifying a fluid medium, particularly of water, having a UV transmission in the range of T (1 cm) 0.9 and greater (1 cm cuvette; wavelength 254 nm) as in any one of claims 19 to 30 wherein the relationship between the irradiation intensity, the character of the medium and the depth of the medium traversed by the irradiation is established so as to correspond to an optimum efficiency in terms of flow-dose rate in adaptation to a medium having a UV transmission T (1 cm) of about 0.9.

35. A process as in any one of claims 19 to 30 wherein the medium is passed through the flow path immediately adjacent to the irradiation source at a linear flow rate above the range of 0.1 and 0.3 meters per second.

36. A process as in claim 31 wherein the medium is passed through the flow path immediately adjacent to the irradiation source at a linear flow rate above the range of 0.1 and 0.3 meters per second.

37. A process as in claim 32 wherein the medium is passed through the flow path immediately adjacent to the irradiation source at a linear flow rate above the range of 0.1 and 0.3 meters per second.

38. A process as in claim 33 wherein the medium is passed through the flow path immediately adjacent to the irradiation source at a linear flow rate above the range of 0.1 and 0.3 meters per second.

39. A process as in any one of claims 19 to 30 wherein the radiation source emits a high power of preferably more than 0.5 watts in the effective wavelength range per centimeter of useful flow path length.

40. A process as in claim 31 wherein the radiation source emits a high power of preferably more than 0.5 watts in the effective wavelength range per centimeter of useful flow path length.

41. A process as in claim 32 wherein the radiation source emits a high power of preferably more than 0.5 watts in the effective wavelength range per centimeter of useful flow path length.

42. A process as in claim 33 wherein the radiation source emits a high power of preferably more than 0.5 watts in the effective wavelength range per centimeter of useful flow path length.

43. A process as in any one of claims 19 to 30 wherein the medium to be irradiated is exposed to a UV radiation dose of preferably at least 12 milliwatt seconds per square centimeter in the flow path immediately adjacent to the radiation source.

44. A process as in claim 31 wherein the medium to be irradiated is exposed to a UV radiation dose of preferably at least 12 milliwatt seconds per square centimeter in the flow path immediately adjacent to the radiation source.

45. A process as in claim 32 wherein the medium to be irradiated is exposed to a UV radiation dose of preferably at least 12 milliwatt seconds per square centimeter in the flow path immediately adjacent to the radiation source.

46. A process as in claim 33 wherein the medium to be irradiated is exposed to a UV radiation dose of preferably at least 12 milliwatt seconds per square centimeter in the flow path immediately adjacent to the radiation source.

47. A process as in claim 34 wherein the medium is passed through the flow path immediately adjacent to the irradiation source at a linear flow rate above the range of 0.1 and 0.3 meters per second.

48. A process as in claim 34 wherein the radiation source emits a high power of preferably more than 0.5 watts in the effective wavelength range per centimeter of useful flow path length.

49. A process as in claim 34 wherein the medium to be irradiated is exposed to a UV radiation dose of preferably at least 12 milliwatt seconds per square centimeter in the flow path immediately adjacent to the radiation source.

* * * * *

UNITED STATES PATENT AND TRADEMARK OFFICE
CERTIFICATE OF CORRECTION

PATENT NO. : 4,296,066
DATED : October 20, 1981
INVENTOR(S) : Gunther Schenck

It is certified that error appears in the above-identified patent and that said Letters Patent are hereby corrected as shown below:

Col. 4, l. 48   "remobably" should be --removable--
Col. 5, l. 31   "$10^{-\epsilon(d_1+2)}$" should be --$10^{-\epsilon(d_1+d_2)}$--
Col. 5, l. 63   "lamps" should be --lamp--
Col. 19, l. 66  "traveresed" should be --traversed--
Col. 21, l. 35  "ranges" should be --range--
Col. 21, l. 61  after "said" first occurrence, insert --one--

Signed and Sealed this

Sixteenth Day of March 1982

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : 4,296,066
DATED : October 20, 1981
INVENTOR(S) : Gunther Schenck

It is certified that error appears in the above-identified patent and that said Letters Patent are hereby corrected as shown below:

Col. 4, l. 48    "removably" should be --removable--

Col. 5, l. 31    "$10^{-\epsilon}(d_1 + {}_2)$" should be --$10^{-\epsilon(d_1 + d_2)}$--

Col. 5, l. 63    "lamps" should be --lamp--
Col. 19, l. 66   "traveresed" should be --traversed--
Col. 21, l. 35   "ranges" should be --range--
Col. 21, l. 61   after "said" first occurrence, insert --one--

This certificate supersedes Certificate of Correction issued March 16, 1982.

Signed and Sealed this

Eighth Day of June 1982

[SEAL]

Attest:

Attesting Officer

GERALD J. MOSSINGHOFF

Commissioner of Patents and Trademarks